United States Patent [19]

Coirault

[11] 4,062,974
[45] Dec. 13, 1977

[54] METHOD FOR TREATING DREPANOCYTOSIS

[75] Inventor: Raymond Coirault, Paris, France

[73] Assignee: Albert Rolland S.A., Chilly Mazarin, France

[21] Appl. No.: 745,546

[22] Filed: Nov. 29, 1976

[51] Int. Cl.$^2$ ............................................ A61K 31/235
[52] U.S. Cl. .................................................... 424/308
[58] Field of Search ................................ 424/311, 308

[56] References Cited

U.S. PATENT DOCUMENTS 3,131,195   4/1964   Rumpf et al. ..................... 424/309

Primary Examiner—Frederick E. Waddell

[57] ABSTRACT

New method for the remedial or prophylactic treatment of drepanocytosis and related syndromes, comprising administering BETA-DIMETHYLAMINO ETHYL ESTER OF PARACHLOROPHENOXY ACETIC ACID or one of its physiologically acceptable acid addition salts, by the IM or oral route.

3 Claims, No Drawings

METHOD FOR TREATING DREPANOCYTOSIS

The present invention relates to a new method for treating the consequences of congenital haemopathies, particularly drepanocytosis and related syndromes, by the remedial or prophylactic administration to the sufferer, of beta-dimethylaminoethyl ester of para-chlorophenoxyacetic acid or one of its physiologically acceptable acid addition salts.

This ester of formula I:

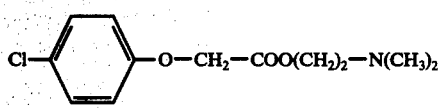

and its preparation are described in U.S. Pat. No. 3,131,195.

Recent studies have shown that, in addition to its stimulant activity on the central nervous system, this compound is useful in the remedial and prophylactic treatment of acute attacks of sickle-cell anaemia in both homozygotes and heterozygotes. The Applicant has made clinical studies which have enabled him to demonstrate this advantageous property. Hereinafter are indicated by way of example the results obtained when the hydrochloride of the compound of formula I was administered by the IM route to a patient suffering a painful attack; each phial contained 250 mg of active ingredient. No phenomenon of intolerance was observed in any case.

EXAMPLE 1

The patient was suffering from a painful osteoarticular attack with appearance of sickle-shaped red blood corpuscles. Two phials of the compound were injected every 6 hours for four days. The pains disappeared in less than 24 hours.

EXAMPLE 2

The patient had a homozygotic form of drepanocytosis and suffered from painful osteoarticular attacks with fever. The treatment consisted in the injection of two phials of the compound every 12 hours for 4 days; the pains disappeared and the fever dropped in less than 3 days.

EXAMPLE 3

The patient had a heterozygotic form of drepanocytosis. An attack, manifesting itself by osteoarticular and abdominal pains and fever, was treated by injection of one phial of the compound every 6 hours for 3 days. The pains disappeared in 24 hours and the fever in less than 3 days.

EXAMPLE 4

The patient, suffering from drepanocytosis, complained of osteoarticular pains. These disappeared less than 3 days after injection of a phial of the compound every 6 hours.

EXAMPLE 5

The patient, suffering from drepanocytosis, complained of articular and violent abdominal pains which disappeared 20 minutes after the injection of a phial of the compound. The treatment was continued for 4 days, at a rate of 3 injections per day.

EXAMPLE 6

The patient, suffering from drepanocytosis, had fever and articular pains. After an IM injection of one phial, every 6 hours, the symptoms disappeared in less than 3 days.

The therapeutic compositions of the invention are prepared by known methods, by association or not of beta-dimethylaminoethyl ester of para-chlorophenoxyacetic acid or one of its salts, with non-toxic excipients. The pharmaceutical forms recommended will be administered either by the oral or IM route.

The injectable form, particularly indicated in the remedial treatment of the attacks, is, for example, as follows:

| | |
|---|---|
| freeze-dried beta-dimethylaminoethyl ester of p.chlorphenoxy acetic acid (hydrochloride) | 250 mg |
| extemporaneous dissolution in sterile water for injection | qsp 5 ml |

Daily dosage is between 1 gram and 2.5 grams according to the seriousness of the attacks and the age of the patient.

Tablets, advantageously used in the prophylactic treatment of the attacks at a rate of 4–6 tablets per day, contain 100 to 250 mg of active ingredient. The following formulation may for example be adopted:

| | |
|---|---|
| beta-dimethylaminoethyl ester of p.chlorophenoxyacetic acid (hydrochloride) | 250 mg |
| tricalcium phosphate | 95 mg |
| talc | 25 mg |
| magnesium stearate | 5 mg |
| polyvinyl acetate | 20 mg | to which are added the protective excipients (ethyl cellulose, dibutyl) phthalate, propylene glycol, white wax, Carnauba wax, spermaceti, methylene chloride and rectified diethyl ether) to obtain a tablet of 400 mg.

What is claimed is:

1. A method for the remedial or prophylactic treatment of attacks suffered by patients having drepanocytosis, comprising administering by the IM or oral route an effective amount of the betadimethylaminoethyl ester of para-chlorophenoxyacetic acid or one of its physiologically acceptable acid addition salts.

2. The method of treatment as defined in claim 1, comprising administering to the patient suffering from a painful attack 1,000 to 2,500 mg of the compound per day, by IM injection.

3. The method of treatment as defined in claim 1, comprising administering to the patient, by way of prevention, from 1,000 to 1,500 mg of the active ingredient per day, preferably by the oral route.

* * * * *